United States Patent [19]

Chen et al.

[11] Patent Number: 5,733,570
[45] Date of Patent: Mar. 31, 1998

US005733570A

[54] ABSORBENT DRESSING

[75] Inventors: Yen-Lane Chen, New Brighton; Chung-I Young, Roseville; Ying-Yuh Lu, Woodbury; Timothy M. Dietz, St. Paul, all of Minn.

[73] Assignee: Minnesota Mining and Manufacturing Company, St. Paul, Minn.

[21] Appl. No.: 709,557

[22] Filed: Sep. 5, 1996

[51] Int. Cl.$^6$ .............................. A61K 9/70; A61L 15/00
[52] U.S. Cl. ............................... 424/445; 424/443
[58] Field of Search ..................... 428/46; 526/264; 424/443, 445, 448, 449

[56] References Cited

U.S. PATENT DOCUMENTS

| | | | |
|---|---|---|---|
| 3,645,835 | 2/1972 | Hodgson | 161/146 |
| 4,231,369 | 11/1980 | Sorensen et al. | 128/283 |
| 4,551,490 | 11/1985 | Doyle et al. | 524/22 |
| 4,595,001 | 6/1986 | Potter et al. | 128/156 |
| 4,693,776 | 9/1987 | Krampe et al. | 156/327 |
| 4,798,201 | 1/1989 | Rawlings et al. | 128/156 |
| 4,952,618 | 8/1990 | Olsen | 524/17 |
| 5,009,224 | 4/1991 | Cole | 128/156 |
| 5,147,698 | 9/1992 | Cole | 428/40 |
| 5,270,358 | 12/1993 | Asmus | 524/55 |
| 5,369,155 | 11/1994 | Asmus | 524/55 |
| 5,407,717 | 4/1995 | Lucast et al. | 428/46 |
| 5,468,821 | 11/1995 | Lucast et al. | 526/264 |
| 5,486,158 | 1/1996 | Samuelsen | 602/46 |
| 5,531,855 | 7/1996 | Heinecke et al. | 156/252 |
| 5,567,430 | 10/1996 | Levy | 424/405 |

FOREIGN PATENT DOCUMENTS

| | | |
|---|---|---|
| 0 272 149 A2 | 6/1988 | European Pat. Off. . |
| 0 437 944 A1 | 7/1991 | European Pat. Off. . |
| 0 591 898 A1 | 4/1994 | European Pat. Off. . |
| WO 84/03837 | 10/1984 | WIPO . |

*Primary Examiner*—Thurman K. Page
*Assistant Examiner*—Kathryne E. Shelborne
*Attorney, Agent, or Firm*—Robert W. Sprague

[57] ABSTRACT

An absorbent dressing that includes a transparent, elastomeric, body fluid-absorbing composition that is essentially free of hydrocolloidal gel particles. The composition includes the reaction product of:

(a) 20 to 80 parts by weight of an acrylic or methacrylic acid ester of a non-tertiary alcohol having between 4 and 14 carbon atoms, inclusive;

(b) 30 to 60 parts by weight of a hydrophilic, ethylenically unsaturated monomer; and p1 (c) 5 to 25 parts by weight of a polar, ethylenically unsaturated monomer different from the hydrophilic, ethylenically unsaturated monomer. The composition is capable of absorbing moderate to heavy amounts of body fluids, while retaining its structural integrity and transparency.

31 Claims, No Drawings

ABSORBENT DRESSING

BACKGROUND OF THE INVENTION

This invention relates to absorbing body fluids, e.g., from wounds.

Various dressings designed for absorbing moderate to heavy amounts of body fluids have been proposed. Such dressings are useful in applications such as wound care, ostomy care, and prosthesis applications. One type of dressing features swellable, hydrocolloidal, gel particles dispersed in a continuous pressure sensitive adhesive matrix. In such dressings, the gel particles absorb body fluids and swell.

SUMMARY OF THE INVENTION

In a first aspect, the invention features an absorbent dressing that includes a transparent, elastomeric, body fluid-absorbing composition that is essentially free of hydrocolloidal gel particles. By "transparent" it is meant that when applied to a patient (e.g., at a wound site), the area underlying the dressing can be visualized sufficiently to permit observation by a health care worker. The composition is capable of absorbing moderate to heavy amounts of body fluids, while retaining its structural integrity (i.e., while remaining sufficiently intact such that it can perform the function of acting as an absorbent dressing) and transparency. The composition includes the reaction product of:

(a) 20 to 80 parts by weight of an acrylic or methacrylic acid ester of a non-tertiary alcohol having between 4 and 14 carbon atoms, inclusive;

(b) 10 to 60 parts by weight of a hydrophilic, ethylenically unsaturated monomer; and (c) 5 to 25 parts by weight of a polar, ethylenically unsaturated monomer different from the hydrophilic, ethylenically unsaturated monomer. By "hydrophilic" it is meant that the monomer has a substantial affinity for water.

In preferred embodiments, the acrylic or methacrylic acid ester is selected from the group consisting of isooctyl acrylate, 2-ethyl hexyl acrylate, butyl acrylate, and combinations thereof. The amount of the acrylic or methacrylic acid ester preferably is less than 50 parts by weight.

The hydrophilic, ethylenically unsaturated monomer preferably is selected from the group consisting of acrylate-terminated poly(alkylene oxides) and methacrylate-terminated poly(alkylene oxides). A preferred monomer is an acrylate-terminated poly(ethylene glycol) monomer. The amount of the hydrophilic, ethylenically unsaturated monomer preferably is between 30 and 60 parts by weight.

The polar, ethylenically unsaturated monomer preferably is selected from the group consisting of acrylic acid, methacrylic acid, itaconic acid, acrylamide, methacrylamide, lower alkyl-substituted acrylamides (e.g., methyl, ethyl and t-butyl-substituted acrylamides), N-vinyl-pyrrolidone, and combinations thereof, with acrylic acid being preferred. The amount of the polar, ethylenically unsaturated monomer preferably is between 15 and 25 parts by weight.

An example of a preferred composition is one that includes the reaction product of isooctyl acrylate, acrylate-terminated poly(ethylene glycol), and acrylic acid. The composition is preferably in the form of a pressure sensitive adhesive. The dressing preferably includes a backing on which the composition is provided.

The composition preferably is capable of absorbing at least about 100%, more preferably at least about 200%, and even more preferably at least about 300% by weight phosphate buffered saline after 24 hours while substantially retaining its structural integrity and transparency.

In a second aspect, the invention features an absorbent dressing that includes a transparent, elastomeric, body fluid-absorbing composition in which the composition includes the reaction product of:

(a) an acrylic or methacrylic acid ester of a non-tertiary alcohol having between 4 and 14 carbon atoms, inclusive;

(b) at least 30 parts by weight of a hydrophilic, ethylenically unsaturated monomer; and (c) a polar, ethylenically unsaturated monomer different from the hydrophilic, ethylenically unsaturated monomer. The composition is capable of absorbing medium to heavy amounts of body fluids while retaining its structural integrity and transparency. Moreover, the composition is essentially free of hydrocolloidal gel particles.

In preferred embodiments, the amount of the hydrophilic, ethylenically unsaturated monomer is between 30 and 60 parts by weight. The composition preferably includes the reaction product of less than 50 parts by weight of the acrylic acid or methacrylic acid ester, 30 to 60 parts by weight of the hydrophilic, ethylenically unsaturated monomer, and 15 to 25 parts by weight of the polar, ethylenically unsaturated monomer. A preferred composition is the reaction product of isooctyl acrylate, acrylate-terminated poly(ethylene glycol), and acrylic acid.

The invention also features a method of treating an exuding wound that includes applying one of the above-described dressing to the wound and allowing the dressing to absorb body fluids exuded from the wound. Furthermore, the invention features transparent, elastomeric, body fluid-absorbing compositions that include the above-described reaction products and have the above-described properties.

In a third aspect, the invention features a method for preparing a transparent, elastomeric, body fluid-absorbing composition that includes exposing an essentially solvent-free monomeric mixture or pre-polymeric syrup to actinic radiation to form the composition. The mixture or syrup includes: (a) an acrylic or methacrylic acid ester of a non-tertiary alcohol having between 4 and 14 carbon atoms, inclusive; (b) a hydrophilic, ethylenically unsaturated monomer; and (c) a polar, ethylenically unsaturated monomer different from the hydrophilic, ethylenically unsaturated monomer. The resulting composition is essentially free of hydrocolloidal gel particles and capable of absorbing moderate to heavy amounts of body fluids while retaining its structural integrity and transparency. In preferred embodiments, the mixture or syrup further includes a photoinitiator and is exposed to ultraviolet radiation.

The invention provides improved dressings based upon transparent, elastomeric, body fluid-absorbing compositions that retain their transparency after absorbing body fluids. The dressings thus permit observation of a wound or ostomy site without requiring removal of the dressing, thereby saving time and money, and avoiding disruption of the healing process. The compositions also display a good balance of absorptive and cohesive properties. Thus, they retain their integrity even after absorbing relatively large amounts of body fluids. Moreover, because the compositions are prepared using a solvent-free, bulk polymerization process, thick compositions can be readily prepared. Such compositions are desirable because fluid absorbency increases with increasing thickness.

Other features and advantages of the invention will be apparent from the following description of the preferred embodiments thereof, and from the claims.

DESCRIPTION OF THE PREFERRED EMBODIMENTS

Transparent, elastomeric, body fluid-absorbing compositions suitable for incorporation in absorbent dressings are prepared from the monomers described in the Summary of the Invention using a photoinitiated, solvent-free, bulk polymerization process. The compositions are preferably in the form of pressure sensitive adhesives to facilitate application to skin. Moreover, the compositions are essentially free of hydrocolloidal gel particles.

The relative amounts of the respective monomers are selected to maximize the fluid absorbency of the composition. At the same time, however, the resulting composition must have sufficient cohesive strength such that it resists disintegrating after absorbing body fluids. Phosphate buffered saline is used as a measure of the composition's performance in the presence of body fluids because it reasonably approximates the composition of body fluids found in wound exudate.

Another important feature of the compositions is the ability to maintain transparency upon absorbing body fluids to the extent that the wound underlying the dressing can be visualized through the dressing. This obviates the need to remove the dressing to observe the underlying wound.

Examples of suitable acrylic and methacrylic acid ester monomers include esters prepared by reaction with alcohols such as 1-butanol, 2-butanol, 1-pentanol, 2-pentanol, 3-pentanol, 2-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctyl alcohol, 2-ethyl-1-hexanol, 1-decanol, 1-dodecanol, 1-tridecanol, 1-tetradecanol, and the like, as well as combinations thereof. Particularly preferred ester monomers include isooctyl acrylate, 2-ethyl hexyl acrylate, and n-butyl acrylate. The amount of ester monomer preferably is less than 50 parts by weight (based upon 100 parts total monomer composition).

Examples of suitable ethylenically unsaturated hydrophilic monomers include free radically reactive hydrophilic oligomers (a polymer having a low number of repeating units, generally 2 to 20) and/or polymers including poly(alkylene oxides) (e.g., poly(ethylene oxide)), poly(vinyl methyl ether), poly(vinyl alcohol), cellulose derivatives, and mixtures thereof. Other suitable ethylenically unsaturated hydrophilic monomers include macromonomers, e.g., acrylate-terminated poly(ethylene oxide), methacrylate-terminated poly(ethylene oxide), methoxy poly(ethylene oxide) methacrylate, butoxy poly(ethylene oxide) methacrylate, p-vinyl benzyl-terminated poly(ethylene oxide), acrylate-terminated poly(ethylene glycol), methacrylate-terminated poly(ethylene glycol), methoxy poly(ethylene glycol) methacrylate, butoxy poly(ethylene glycol) methacrylate, p-vinyl benzyl-terminated poly(ethylene glycol), poly(ethylene oxide) diacrylate, poly(ethylene oxide) dimethacrylate, and combinations thereof. Particularly preferred ethylenically unsaturated hydrophilic monomers include acrylate and methacrylate esters prepared from mono-hydroxyl-terminated poly(lower alkylene oxides) such as polyethylene and polypropylene glycols commercially available under the trade designation Carbowax from Union Carbide Corp. in a variety of molecular weights (e.g., Carbowax 350, Carbowax 550, Carbowax 750, Carbowax 2000, and Carbowax 5000). An example of a preferred acrylate-terminated polyethylene glycol is commercially available from Shin-Nakamura Chemical Co., Ltd., Japan, under the designation "NK Ester AM-90G."

The amount of hydrophilic monomer preferably ranges from 30 to 60 parts by weight (based upon 100 parts total monomer composition).

Examples of suitable polar monomers include acrylic acid, methacrylic acid, itaconic acid, acrylamide, methacrylamide, lower alkyl-substituted acrylamides (e.g., methyl, ethyl and t-butyl-substituted acrylamides), N-vinyl-pyrrolidone, and combinations thereof. The preferred polar monomer is acrylic acid. The amount of polar monomer preferably ranges from 15 to 25 parts by weight (based upon 100 parts total monomer composition).

One or more multifunctional crosslinking monomers may be included as well. The term "multifunctional" as used herein refers to crosslinking monomers which have two or more free radically polymerizable, ethylenically unsaturated groups. Useful multi-functional crosslinking monomers include acrylic or methacrylic esters of diols such as butanediol diacrylate, triols such as glycerol, and tetraols such as pentaerythritol. Other useful multifunctional crosslinking monomers include polymeric multifunctional (meth) acrylates, e.g., poly(ethylene oxide) diacrylate or poly(ethylene oxide) dimethacrylate; polyvinylic crosslinking agents such as substituted and unsubstituted divinylbenzene; and difunctional urethane acrylates such as "EBECRYL" 270 and "EBECRYL" 230 (1500 weight average molecular weight and 5000 weight average molecular weight acrylated urethanes, respectively-both available from Radcure Specialties), and combinations thereof.

When a crosslinking monomer is employed, the amount is selected such that the fluid absorbency of the composition is not substantially compromised. In general, the crosslinking monomer (when present) is employed at a level of up to about 10 equivalent weight percent. The "equivalent weight percent" of a given compound is defined as the number of equivalents of that compound divided by the total number of equivalents in the total monomer composition, where an equivalent is the number of grams divided by the equivalent weight. The equivalent weight is defined as the molecular weight divided by the number of polymerizable groups in the monomer (in the case of those monomers with only one polymerizable group, equivalent weight equals molecular weight).

A photoinitiator is included in the monomer mixture as well. Useful photoinitiators include substituted acetophenones such a benzyl dimethyl ketal and 1-hydroxycyclohexyl phenyl ketone, substituted alpha-ketols such as 2-methyl-2-hydroxypropiophenone, benzoin ethers such as benzoin methyl ether, benzoin isopropyl ether, substituted benzoin ethers such as anisoin methyl ether, aromatic sulfonyl chlorides, and photoactive oximes. The amount of photoinitiator typically ranges from about 0.001 to about 5.0 parts by weight per 100 parts of total monomer, preferably from about 0.01 to about 5.0 parts by weight, and more preferably from about 0.1 to about 0.5 parts by weight.

Other materials which may be added to the monomer mixture include chain transfer agents for controlling molecular weight (e.g., carbon tetrabromide, mercaptans, or alcohols), tackifiers, plasticizers (e.g., polyethylene glycol, polypropylene glycol, or glycerin), perfumes, deodorants, antioxidants, and pharmacologically active ingredients such as drugs, antibiotics, and anti-microbial agents.

The compositions are prepared by photoinitiated bulk polymerization according to the technique described in Martens et al., U.S. Pat. No. 4,181,752, hereby incorporated by reference. The polymerizable monomers and photoinitiator are mixed together in the absence of solvent and partially polymerized to a viscosity in the range of from about 500 cps to about 50,000 cps to achieve a coatable syrup. The crosslinking agent (if present) and any other ingredients are then added to the prepolymerized syrup. Alternatively, these ingredients (with the exception of the crosslinking agent) can be added directly to the monomer mixture prior to pre-polymerization.

The resulting composition is coated onto a substrate (which may be transparent to ultraviolet radiation) and polymerized in an inert (i.e., oxygen-free) atmosphere, e.g., a nitrogen atmosphere by exposure to ultraviolet radiation. Examples of suitable substrates include release liners (e.g., silicone release liners) and tape backings (which may be primed or unprimed paper or plastic). A sufficiently inert atmosphere can also be achieved by covering a layer of the polymerizable coating with a plastic film which is substantially transparent to ultraviolet radiation, and irradiating through that film in air, as described in the aforementioned Martens et al. patent using ultraviolet lamps. The ultraviolet light source preferably has 60% of its emissions, and more preferably at least 75% of its emissions, between 280 and 400 nm, with an intensity ranging from about 0.1 to about 25 mW/cm$^2$.

Where multi-layer constructions are desirable, one method of construction is multi-layer coating using conventional techniques. For example, the coatings may be applied concurrently (e.g., through a die coater), after which the entire multi-layer structure is cured all at once. The coatings may also be applied sequentially whereby each individual layer is partially or completely cured prior to application of the next layer.

The compositions can be included in a variety of dressing constructions known in the art. Typically, the composition is in the form of a continuous or discontinuous coating on at least one major surface of a backing. The backing may include one or more layers. Examples of suitable backings include materials with a relatively low content of hydrophilic components such as polyester (e.g., commercially available under the designation "Hytrel™," such as Hytrel™ 4056, from DuPont Co.), polyurethane (e.g., commercially available under the designation "Estane™," such as Estane™ 58309, from B.F. Goodrich Co.), polyester block amide (e.g., commercially available under the designation "Pebax™," such as Pebax™ 2533 and 3533, from Atochem Co.), and porous polyethylene resins. Also suitable are materials having a relatively high content of hydrophilic components (and thus high moisture vapor transmission properties). Examples include certain polyester amides such as Pebax™ 4011RN00 (Atochem Co.), porous polyethylenes as described in U.S. Pat. No. 4,539,256, and polyrethanes described in U.S. Pat. Nos. 3,645,535 and 4,598,004. Both classes of materials may also be used in combination with each other (e.g., in sandwich-type arrangements) to tailor the moisture vapor transmission properties of the dressing.

Examples of specific dressing configurations for which the compositions are suitable are described in Olson, U.S. Pat. No. 4,952,618, hereby incorporated by reference.

The invention will now be further described by way of the following examples.

EXAMPLES

General Polymerization Process

A vial was charged with isooctylacrylate, after which 0.04% by weight photoinitiator (benzyl dimethyl ketal) was added and stirred until dissolution. Acrylic acid and polyethylene glycol acrylate ("NK Ester-AM-90G" from Shin-Nakamura Chemical Co., Ltd., Japan) were then added to the solution and the resulting solution reacted to form a pre-polymerized syrup. A second portion of photoinitiator was added to the syrup, after which the syrup was coated between two release liners; the total amount of photoinitiator used was 0.4% by weight of the total monomer weight. One of the release liners was typically a clear polyethylene terephthalate film and the other liner was either paper or a second polyethylene terephthalate film. The caliper was set at 40–45 mils for each sample during the coating process.

Following coating, the sample was cured by exposure to a series of ultraviolet black lights (Sylvania Corp.) at a peak wavelength of 350 nm and an intensity of 40W.

Test Methods

Absorbency

A preweighed sample of the composition ($W_i$) was placed in a 6 oz. (180 mL) bottle containing 30 mL of phosphate buffered saline (PBS, pH=7.2) (Sigma Chemical Co.). The bottle was capped and allowed to stand without agitation. Samples were removed intermittently at fixed intervals, blotted dry, and weighed. A final weight ($W_e$) was obtained after 24 hours of exposure. The absorbency was calculated using the following formula:

$$\text{Absorbency} = (W_e - W_i)/W_i$$

Absorbency data is reported in Table 1.

Moisture Vapor Transmission Rate

The moisture vapor transmission rate was measured according to ASTM E-96-80 using a modified Payne cup method. Specifically, a 35 mm diameter sample of 1 mil (0.025 mm) thick material to be tested containing no perforations was cut. The sample was placed between adhesive-containing surfaces of two foil adhesive rings, each having a one inch (2.54 cm) diameter hole. The holes of each ring were carefully aligned. Finger pressure was used to form a foil/sample/foil assembly that was flat, wrinkle-free, and had no void areas in the exposed sample.

A 4 oz. (0.14 kg) glass jar was filled half-way with distilled water. The jar was fitted with a screw-on cap having a 1.50 inch (3.8 cm) diameter hole in the center thereof and with a 1.75 inch (4.45 cm) diameter rubber washer having a 1.12 inch (2.84 cm) diameter hole in its center. The rubber washer was placed on the lip of the jar and the foil/sample assembly was placed on the rubber washer. The lid was then screwed loosely on the jar.

The assembly was placed in a chamber at 100° F. (38° C.) and 20% relative humidity for four hours. The cap was tightened inside the chamber so that the sample was level with the cap (no bulging) and the rubber washer was in proper seating position.

At the end of four hours, the foil/sample assembly was removed from the chamber and weighed immediately to the nearest 0.01 gram (initial weight $W_1$). The assembly was then returned to the chamber for at least 18 hours, after which it was removed and weighed immediately to the nearest 0.01 gram (final weight $W_2$). The moisture vapor transmission rate (MVTR) in grams of water vapor transmitted per square meter of sample area in 24 hours was calculated according to the following formula (where "T" refers to exposure time in hours):

$$MVTR = (W_1 - W_2)(4.74 \times 10^4)/T$$

Three measurements of each sample were made, and the average value taken. The MVTR values are reported in Table 2 in g/m$^2$/24 hrs.

Skin Adhesion

Adhesion to skin was determined utilizing dressings prepared using the compositions prepared in Examples 1–7. The laminate dressings were cut into 2.5 cm×7.5 cm strips which were then applied to the backs (left side=dry; right side=wet) of a selected number of individuals. During application and removal of the test strips, the individuals were lying on procedure tables in prone positions with arms at their sides and heads turned to one side. For each individual, two or three strips of the test material were applied on each of the sides of the spinal column and positioned such that the length of each strip was at a right angle to the spinal column. The strips were applied without tension or pulling of the skin, and there was at least 0.3 cm to 1 cm space between each strip. After all strips were in place, a 2 kg rubber roller according to the specifications found in the 7th Edition of the Pressure-Sensitive Tape Council Brochure (1976) was rolled along the length of each strip, once in each direction, at a travel speed of about 7.6 cm per second, to assure even pressure application of each strip. When rolling the strip, no manual pressure was applied to the roller.

To determine the adhesive value, each strip was removed using a conventional adhesion tester having a 11.4 kg test line and a 2.5 cm clip attached to the test line. The clip was attached to the edge of the strip which is farthest from the spinal cord, the clip being attached by manually lifting about 1 cm of that edge of the strip and attaching the clip thereto. This orientation permitted the strip to be removed towards the spine so that pull was with the direction of the hair growth on the back. This was facilitated bypositioning the adhesion tester opposite the side of the individual's back from which the strip was to be removed. The adhesion tester was aligned with, and was at the same height as, the strip to be removed. An example of a suitable adhesion tester for use in this test comprises a conventional motor driven screw with moving carriage and a transducer. Connection to the transducer was a load cell accessory. Removal force placed on the transducer resulted in a signal change which was passed through a readout meter to a strip chart recorder.

Wet and dry skin adhesion data is reported in Table 3 in gm/2.54 cm. Dry adhesion values were determined initially ($T_0$) and after 24 hours ($T_{24}$). Wet adhesion values were determined initially ($T_0$).

Integrity

A preweighed sample of the composition ($W_i$) in the form of a 5 cm disc was placed in a 6 oz. (180 mL) bottle containing 30 mL of phosphate buffered saline (PBS, pH=7.2) (Sigma Chemical Co.). The bottle was capped and agitated on a shaker (Eberbach Co., Ann Arbor, MI) at low speed for a period of 24 hours. The sample was then removed from the bottle, transferred to a metal pan, and dried in a forced-air oven maintained at 65°C. until dry (typically about 12–16 hours). Following drying, the sample was weighed ($W_f$). The Integrity Value was calculated according to the following formula:

Integrity Value=$W_f/W_i$33 100

Integrity data is reported in Table 4.

Example 1

A composition was prepared using 80 parts isooctyl acrylate, 6.0 parts acrylic acid, and 14.0 parts polyethylene glycol acrylate, and tested according to the above-described test methods. Test results are shown in Tables 1–4.

Example 2

A composition was prepared using 70 parts isooctyl acrylate, 9.0 parts acrylic acid, and 21.0 parts polyethylene glycol acrylate, and tested according to the above-described test methods. Test results are shown in Tables 1–4.

Example 3

A composition was prepared using 60 parts isooctyl acrylate, 12.0 parts acrylic acid, and 28.0 parts polyethylene glycol acrylate, and tested according to the above-described test methods. Test results are shown in Tables 1–4.

Example 4

A composition was prepared using 50 parts isooctyl acrylate, 15.0 parts acrylic acid, and 35.0 parts polyethylene glycol acrylate, and tested according to the above-described test methods. Test results are shown in Tables 1–4.

Example 5

A composition was prepared using 40 parts isooctyl acrylate, 18.0 parts acrylic acid, and 42.0 parts polyethylene glycol acrylate, and tested according to the above-described test methods. Test results are shown in Tables 1–4.

Example 6

A composition was prepared using 30 parts isooctyl acrylate, 21.0 parts acrylic acid, and 49.0 parts polyethylene glycol acrylate, and tested according to the above-described test methods. Test results are shown in Tables 1–4.

Example 7

A composition was prepared using 20 parts isooctyl acrylate, 24.0 parts acrylic acid, and 56.0 parts polyethylene glycol acrylate, and tested according to the above-described test methods. Test results are shown in Tables 1–4.

TABLE 1

| ABSORBENCY | |
| --- | --- |
| EXAMPLE | Amount of PBS Absorbed (@ 24 hrs) |
| 1 | 0.231 |
| 2 | 1.662 |
| 3 | 2.308 |
| 4 | 5.316 |
| 5 | 8.060 |
| 6 | 8.587 |
| 7 | 12.132 |

TABLE 2

| MOISTURE VAPOR TRANSMISSION RATE (G/M²/DAY) | |
| --- | --- |
| EXAMPLE | MVTR (G/M²/DAY) |
| 1 | 1432 |
| 2 | 1855 |
| 3 | 4668 |
| 4 | 6754 |
| 5 | 6685 |
| 6 | 6035 |
| 7 | 6395 |

TABLE 3

SKIN ADHESION (GM/2.54 CM)

| EXAMPLE | Adhesion (gm/2.54 cm) | | |
|---|---|---|---|
| | Dry $T_0$ | $T_{24}$ | Wet $T_0$ |
| 1 | 379 | 667 | 224 |
| 2 | 183 | 433 | 116 |
| 3 | 112 | 254 | 55 |
| 4 | 101 | 262 | 43 |
| 5 | 55 | 104 | 61 |
| 6 | 25 | 46 | 27 |
| 7 | 30 | 211 | 43 |

TABLE 4

INTEGRITY

| EXAMPLE | INTEGRITY |
|---|---|
| 3 | 99.3% |
| 4 | 98.6% |
| 5 | 97.4% |

Other embodiments are within the following claims.

What is claimed is:

1. An absorbent dressing comprising a transparent, elastomeric, body fluid-absorbing composition, said composition comprising the reaction product of:
(a) 20 to 80 parts by weight of an acrylic or methacrylic acid ester of a non-tertiary alcohol having between 4 and 14 carbon atoms, inclusive;
(b) 10 to 60 parts by weight of a hydrophilic, ethylenically unsaturated monomer; and
(c) 5 to 25 parts by weight of a polar, ethylenically unsaturated, carboxylic acid-containing monomer different from said hydrophilic, ethylenically unsaturated monomer, said composition being capable of absorbing moderate to heavy amounts of body fluids while retaining its structural integrity and transparency, said composition being essentially free of hydrocolloidal gel particles.

2. An absorbent dressing according to claim 1 wherein said acrylic or methacrylic acid ester is selected from the group consisting of isooctyl acrylate, 2-ethyl hexyl acrylate, butyl acrylate, and combinations thereof.

3. An absorbent dressing according to claim 1 wherein said hydrophilic, ethylenically unsaturated monomer is selected from the group consisting of acrylate-terminated poly(alkylene oxides) and methacrylate-terminated poly (alkylene oxides).

4. An absorbent dressing according to claim 1 wherein said hydrophilic, ethylenically unsaturated monomer comprises an acrylate-terminated poly(ethylene glycol) monomer.

5. An absorbent dressing according to claim 1 wherein said polar, ethylenically unsaturated monomer is selected from the group consisting of acrylic acid, methacrylic acid, itaconic acid, and combinations thereof.

6. An absorbent dressing according to claim 1 wherein said polar, ethylenically unsaturated monomer comprises acrylic acid.

7. An absorbent dressing according to claim 1 wherein the amount of said acrylic acid or methacrylic acid ester is less than 50 parts by weight.

8. An absorbent dressing according to claim 1 wherein the amount of said hydrophilic, ethylenically unsaturated monomer is between 30 and 60 parts by weight.

9. An absorbent dressing according to claim 1 wherein the amount of said polar, ethylenically unsaturated monomer is between 15 and 25 parts by weight.

10. An absorbent dressing according to claim 1 wherein said composition comprises the reaction product of isooctyl acrylate, acrylate-terminated poly(ethylene glycol), and acrylic acid.

11. An absorbent dressing according to claim 1 wherein said composition comprises the reaction product of less than 50 parts by weight of said acrylic acid or methacrylic acid ester, 30 to 60 parts by weight of said hydrophilic, ethylenically unsaturated monomer, and 15 to 25 parts by weight of said polar, ethylenically unsaturated monomer.

12. An absorbent dressing according to claim 1 wherein said composition is capable of absorbing at least about 100% by weight phosphate buffered saline after 24 hours while substantially retaining its structural integrity and transparency.

13. An absorbent dressing according to claim 1 wherein said composition is capable of absorbing at least about 200% by weight phosphate buffered saline after 24 hours while substantially retaining its structural integrity and transparency.

14. An absorbent dressing according to claim 1 wherein said composition is capable of absorbing at least about 300% by weight phosphate buffered saline after 24 hours while substantially retaining its structural integrity and transparency.

15. An absorbent dressing according to claim 1 wherein said composition is in the form of a pressure sensitive adhesive.

16. An absorbent dressing according to claim 1 further comprising a backing on which said composition is provided.

17. An absorbent dressing comprising a transparent, elastomeric, body fluid-absorbing composition, said composition comprising the reaction product of:
(a) an acrylic or methacrylic acid ester of a non-tertiary alcohol having between 4 and 14 carbon atoms, inclusive;
(b) at least 30 parts by weight of a hydrophilic, ethylenically unsaturated monomer; and
(c) a polar, ethylenically unsaturated, carboxylic acid-containing monomer different from said hydrophilic, ethylenically unsaturated monomer, said composition being capable of absorbing moderate to heavy amounts of body fluids while retaining its structural integrity and transparency, said composition being essentially free of hydrocolloidal gel particles.

18. An absorbent dressing according to claim 17 wherein the amount of said hydrophilic, ethylenically unsaturated monomer is between 30 and 60 parts by weight.

19. An absorbent dressing according to claim 17 wherein said composition comprises the reaction product of less than 50 parts by weight of said acrylic acid or methacrylic acid ester, 30 to 60 parts by weight of said hydrophilic, ethylenically unsaturated monomer, and 15 to 25 parts by weight of said polar, ethylenically unsaturated monomer.

20. An absorbent dressing according to claim 17 wherein said composition comprises the reaction product of isooctyl acrylate, acrylate-terminated poly(ethylene glycol), and acrylic acid.

21. A method of treating an exuding wound comprising applying a dressing to said wound and allowing said dressing to absorb body fluids exuded from said wound, said dressing comprising a transparent, elastomeric, body fluid-absorbing composition, said composition comprising the reaction product of:
(a) 20 to 80 parts by weight of an acrylic or methacrylic acid ester of a non-tertiary alcohol having between 4 and 14 carbon atoms, inclusive;
(b) 10 to 60 parts by weight of a hydrophilic, ethylenically unsaturated monomer; and
(c) 5 to 25 parts by weight of a polar, ethylenically unsaturated, carboxylic acid-containing monomer different from said hydrophilic, ethylenically unsaturated monomer, said composition being capable of absorbing moderate to heavy amounts of body fluids while retaining its structural integrity and transparency, said composition being essentially free of hydrocolloidal gel particles.

22. A method according to claim 21 wherein the amount of said acrylic acid or methacrylic acid ester is less than 50 parts by weight.

23. A method according to claim 21 wherein the amount of said hydrophilic, ethylenically unsaturated monomer is between 30 and 60 parts by weight.

24. A method according to claim 21 wherein the amount of said polar, ethylenically unsaturated monomer is between 15 and 25 parts by weight.

25. A method of treating an exuding wound comprising applying a dressing to said wound and allowing said dressing to absorb body fluids exuded from said wound, said dressing comprising a transparent, elastomeric, body fluid-absorbing composition, said composition comprising the reaction product of:
(a) an acrylic or methacrylic acid ester of a non-tertiary alcohol having between 4 and 14 carbon atoms, inclusive;
(b) at least 30 parts by weight of a hydrophilic, ethylenically unsaturated monomer; and
(c) a polar, ethylenically unsaturated, carboxylic acid-containing monomer different from said hydrophilic, ethylenically unsaturated monomer, said composition being capable of absorbing moderate to heavy amounts of body fluids while retaining its structural integrity and transparency, said composition being essentially free of hydrocolloidal gel particles.

26. A method according to claim 25 wherein the amount of said hydrophilic, ethylenically unsaturated monomer is between 30 and 60 parts by weight.

27. A method according to claim 25 wherein said composition comprises the reaction product of less than 50 parts by weight of said acrylic acid or methacrylic acid ester, 30 to 60 parts by weight of said hydrophilic, ethylenically unsaturated monomer, and 15 to 25 parts by weight of said polar, ethylenically unsaturated monomer.

28. A transparent, elastomeric, body fluid-absorbing composition, said composition comprising the reaction product of:
(a) 20 to 80 parts by weight of an acrylic or methacrylic acid ester of a non-tertiary alcohol having between 4 and 14 carbon atoms, inclusive;
(b) 10 to 60 parts by weight of a hydrophilic, ethylenically unsaturated monomer; and
(c) 5 to 25 parts by weight of a polar, ethylenically unsaturated, carboxylic acid-containing monomer different from said hydrophilic, ethylenically unsaturated monomer, said composition being capable of absorbing moderate to heavy amounts of body fluids while retaining its structural integrity and transparency, said composition being essentially free of hydrocolloidal gel particles.

29. A transparent, elastomeric, body fluid-absorbing composition, said composition comprising the reaction product of:
(a) an acrylic or methacrylic acid ester of a non-tertiary alcohol having between 4 and 14 carbon atoms, inclusive;
(b) at least 30 parts by weight of a hydrophilic, ethylenically unsaturated monomer; and
(c) a polar, ethylenically unsaturated, carboxylic acid-containing monomer different from said hydrophilic, ethylenically unsaturated monomer, said composition being capable of absorbing moderate to heavy amounts of body fluids while retaining its structural integrity and transparency, said composition being essentially free of hydrocolloidal gel particles.

30. A method for preparing a transparent, elastomeric, body fluid-absorbing composition comprising exposing an essentially solvent-free monomeric mixture or pre-polymeric syrup to actinic radiation to form said composition, said mixture or syrup comprising:
(a) an acrylic or methacrylic acid ester of a non-tertiary alcohol having between 4 and 14 carbon atoms, inclusive;
(b) a hydrophilic, ethylenically unsaturated monomer; and
(c) a polar, ethylenically unsaturated monomer different from said hydrophilic, ethylenically unsaturated monomer, said composition being essentially free of hydrocolloidal gel particles and capable of absorbing moderate to heavy amounts of body fluids while retaining its structural integrity and transparency.

31. A method according to claim 30 wherein said mixture or syrup further comprises a photoinitiator and said method comprises exposing said mixture or syrup to ultraviolet radiation.

* * * * *